United States Patent
Weidner

(10) Patent No.: US 6,217,877 B1
(45) Date of Patent: Apr. 17, 2001

(54) PHARMACEUTICAL COMPOSITIONS CONTAINING PARTHENIUM INTEGRIFOLIUM OR PARTS THEREOF OR AN EXTRACT OR COMPONENT THEREOF, THE USE OF SUCH PLANT MATERIAL FOR PREPARING CERTAIN MEDICINES, AND A METHOD OF PREPARING AN EXTRACT OF PARTHENIUM INTEGRIFOLIUM

(76) Inventor: Morten Sloth Weidner, Solbakken 7, Virum (DK), DK-2830

( * ) Notice: Subject to any disclaimer, the term of this patent is extended or adjusted under 35 U.S.C. 154(b) by 0 days.

(21) Appl. No.: 09/299,104

(22) Filed: Apr. 21, 1999

Related U.S. Application Data

(63) Continuation of application No. PCT/DK97/00457, filed on Oct. 20, 1997.
(60) Provisional application No. 60/031,395, filed on Nov. 19, 1996.

(30) Foreign Application Priority Data

Oct. 21, 1996 (DK) .................................................. 1158/96

(51) Int. Cl.$^7$ ................................................... A61K 35/78
(52) U.S. Cl. .......................................................... 424/195.1
(58) Field of Search .......................................... 424/195.1

(56) References Cited

U.S. PATENT DOCUMENTS

| 4,058,594 | * | 11/1977 | Williams . |
| 4,758,433 | | 7/1988 | Johnson et al. . |
| 5,053,387 | * | 10/1991 | Alexander . |
| 5,055,297 | * | 10/1991 | Fujimaki et al. . |

FOREIGN PATENT DOCUMENTS

3638715 A1    5/1988   (DE) .

OTHER PUBLICATIONS

Derwent English abstract of German Pat. No. 3,638,715 A, May 1988.*
Croom, E.M. et al., Drug Topics, pp. 84–91, Nov. 6, 1995.

* cited by examiner

Primary Examiner—Francisco Prats
Assistant Examiner—Susan D. Coe
(74) Attorney, Agent, or Firm—Darby & Darby

(57) ABSTRACT

The use of *Parthenium integrifolium* (PI) or its parts, extract or components, for enhancement of the TH2 pathway of the immune system, enhancement of levels of interleukin-4 and -10, and selective suppression of cyclooxygenase-2. Also claimed are: (1) composition containing PI; and (2) extracts of PI and their preparation. PI is particularly useful for alleviation of pain (e.g. migraine or headache), and treatment or prevention of inflammatory or autoimmune disorders.

6 Claims, No Drawings

PHARMACEUTICAL COMPOSITIONS CONTAINING PARTHENIUM INTEGRIFOLIUM OR PARTS THEREOF OR AN EXTRACT OR COMPONENT THEREOF, THE USE OF SUCH PLANT MATERIAL FOR PREPARING CERTAIN MEDICINES, AND A METHOD OF PREPARING AN EXTRACT OF PARTHENIUM INTEGRIFOLIUM

This is a continuation of International Application No. PCT/DK97/00457, filed Oct. 20. 1997, which claims priority of U.S. Provisional application Ser. No. 60/031,395, filed Nov. 19, 1996.

FIELD OF THE INVENTION

The present invention relates to the plant *Parthenium integrifolium* and more specifically to pharmaceutical compositions derived from it as well as the use of *Parthenium integrifolium* or parts thereof or an extract or component thereof for the preparation of medicines for the alleviation of pain or for the treatment or prevention of inflammatory or autoimmune disorders. The invention also relates to a method of preparing an extract of *Parthenium integrifolium* and to the extracts prepared by the method.

BACKGROUND OF THE INVENTION

*Parthenium integrifolium* (L.) (family Asteraceae), also commonly known as Missouri snake root, grows wild in woodland and prairies of North America. The herb is 30–130 cm high with numerous white flowerheads forming a flat inflorescence up to 25 cm wide. The root is comprised of a short, conical or bulbshaped headstem that has a diameter of up to 4 cm and elongated secondary, twisted branches leading from the headstem.

A number of chemicals have been identified as major components of *Parthenium integrifolium* extracts. One group are the sesquiterpene lactones represented by tetraneurin E and tetraneurin C. Another group are the sesquiterpene esters represented by echinadiol cinnamate, epoxy echinadiol cinnamate, echinaxanthol cinnamate and dihydroxynardol cinnamate. Yet another group are the flavonoids represented by quercetagetin methyl ethers and their O-glycosides. Another characteristic component of *Parthenium integrifolium* is pyromeconic acid. Other chemicals present in the plant are coumarins and diverse phenolic glycosides.

The German patent application, publication no. 36 38 715 A1 describes the above mentioned sesquiterpene esters derived from *Parthenium integrifolium*. According to the experimental section of that application, immunological activity tests of the sesquiterpene esters showed that they enhanced granulocyte phagocytosis in vitro up to 30%. This effect is to be considered a pro-inflammatory action related to the non-specific part of the immune system (the reticuloendothelial phagocytic system).

At present the nonsteroidal antiinflammatory drugs (NSAIDS) are the most commonly applied therapeutic agents for the treatment of conditions associated with inflammation and pain. The NSAIDs exert their action by inhibiting the prostaglandin-generating enzyme cyclooxygenase (COX). There are two biochemical subtypes of cyclooxygenase denominated COX-1 and COX-2. COX-1 is constitutively expressed in most cells and is responsible for the formation of prostaglandins which mediate important basic physiological functions, e.g. providing an intact mucosa in the ventricle. COX-2 is not normally present, but may be induced by certain serum factors, cytokines and growth factors and responsible for the formation of inflammatory prostaglandins which mediate many symptoms of inflammation. The NSAIDs are generally non-selective, meaning that they inhibit both COX-2 and COX-1 resulting in an antiinflammatory and pain relieving effect due to the inhibition of COX-2 and a number of side effects due to the inhibition of COX-1, of which gastric ulceration is one of the most important.

Autoimmune disorders like multiple sclerosis, morbus Crohn, rheumatoid arthritis, diabetes mellitus, etc. are associated with an overactivation of the inflammatory arm of the immune system ($T_H1$ pathway) leading to well known symptoms and serious tissue destruction. The most well established treatment for these disorders is the management of corticosteroids which exert their action by non-selectively inhibiting the function and proliferation of different types of immune cells. Unfortunately the corticosteroids are associated with a number of serious side effects e.g. immunosuppression and osteoporosis.

SUMMARY OF THE INVENTION

I have found that *Parthenium integrifolium* or parts thereof or an extract or component thereof exert the following pharmacological actions: Enhancement of the $T_H2$ pathway of the immune system, enhancement of the levels of interleukin-4 and interleukin-10, suppression of cyclooxygenase-2 (COX-2), reduction of chronic and acute pain, and reduction of inflammation. Compared to the NSAIDs *Parthenium integrifolium* or parts thereof or an extract or component thereof have the advantage that they are not associated with gastrointestinal and renal side effects. Further, by enhancing the formation of interleukin-4 and interleukin-10 they have a down regulating effect on the $T_H1$ pathway of the immune system without exerting the serious side effects characteristic of the corticosteroids. Due to these effects *Parthenium integrifolium* or parts thereof or an extract or component thereof can be employed for the following therapeutic applications:

Alleviation of pain.

Treatment or prevention of inflammatory or autoimmune disorders.

Accordingly the present invention provides a pharmaceutical composition containing *Parthenium integrifolium* or parts thereof or an extract or component thereof and a pharmaceutically acceptable carrier.

More specifically the present invention provides the use of *Parthenium integrifolium* or parts thereof or an extract or component thereof for preparing a medicine for the enhancement of the $T_H2$ pathway of the immune system, for the enhancement of the levels of interleukin-4 and interleukin-10, and for the selective suppression of COX-2.

Thus, according to the invention *Parthenium integrifolium* or parts thereof or an extract or component thereof can be used in a method for the alleviation of pain in an individual, which comprises administering such plant material or a pharmaceutical composition containing it to said individual; and the invention comprises the use of *Parthenium integrifolium* or parts thereof or an extract or component thereof for preparing a medicine for the alleviation of pain.

Also, according to the invention *Parthenium integrifolium* or parts thereof or an extract or component thereof can be used in a method for the treatment or prevention of an inflammatory or autoimmune disorder in an individual, which comprises administering such plant material or a pharmaceutical composition containing it to said individual; and the invention comprises the use of *Parthenium integrifolium* or parts thereof or an extract or component thereof for preparing a medicine for the treatment or prevention of inflammatory or autoimmune disorders.

Further, the invention provides a method of preparing an extract of *Parthenium integrifolium*, which comprises extracting said plant or parts thereof, preferably the root, with an extraction agent comprising an organic solvent or a mixture thereof with water and subsequently, if necessary, removing the extraction agent to obtain an extract suitable for utilisation.

DETAILED DESCRIPTION OF THE INVENTION

Surprisingly it has been found that *Parthenium integrifolium* or parts thereof or an extract or component thereof exert pharmacological actions relevant to the therapeutic treatment of conditions associated with pain, inflammation and autoimmunity.

More specifically *Parthenium integrifolium* or parts thereof or an extract or component thereof provide the following pharmacological effects upon administration to the living organism:

Enhancement of the $T_H2$ pathway of the immune system.

Enhancement of the levels of interleukin-4 and interleukin-10.

Suppression of COX-2 without affecting COX-1.

Reduction of pain.

Reduction of inflammation.

These actions provide part of the rationale for the following therapeutic applications of *Parthenium integrifolium* or parts thereof or extracts or components thereof:

A method for the treatment of any condition associated with pain or inflammation characterised by the administration of *Parthenium integrifolium* or parts thereof or an extract or component thereof. The applicant puts forward the hypothesis that the antiinflammatory and pain relieving action is due to enhanced levels of interleukin-4 and -10 which on one hand down regulate the inflammatory part of the immune system ($T_H1$ pathway) and on the other hand reduce the expression of COX-2 leading to a lower level of inflammatory prostaglandins. This mechanism of action holds the advantage compared to conventional nonsteroidal antiinflammatory drugs (NSAIDs) that COX-1 is not inhibited whereby gastric ulceration and renal side effects are avoided. In a preliminary clinical observation a patient with pain and inflammation due to osteoarthritis in the lower back experienced a significant improvement after treatment with 250 mg a day of the extract of *Parthenium integrifolium* described in example 1. The patient was subjected to an oral dose of 125 mg of the extract twice a day, administered in a hard gelatine capsule. The improvement which consisted in a total elimination of pain and increased mobility in the affected joints was apparent on day 2 of treatment and continued for the entire period of treatment during 3 weeks. After termination of the treatment the pain returned after two days. The clinical improvement is attributed to the above mentioned effects of *Parthenium integrifolium*. In the clinical pilot study described in example 4 patients (n=16) suffering from migraine headache were subjected to a daily dose of an extract of *Parthenium integrifolium*. The study schedule consisted of four periods of four weeks. The first period served as a baseline, where no treatment was employed. In the second period a daily dose of 200 mg *Parthenium integrifolium* extract was employed. In the third period a daily dose of 100 mg *Parthenium integrifolium* extract was employed. In the fourth period a daily dose of 200 mg *Parthenium integrifolium* extract was employed. During the four periods all incidences of migraine headache were recorded. The incidence of migraine headache was reduced in all of the treatment periods as compared to the baseline period. In the last treatment period the incidence of migraine headache was reduced by 57%, which was statistically significant ($p<0,05$; Wilcoxon). The observed clinical improvement is attributed to the above mentioned effects of *Parthenium integrifolium*.

A method for the treatment of inflammatory and autoimmune disorders characterised by the administration of *Parthenium integrifolium* or parts thereof or an extract or component thereof. The applicant puts forward the hypothesis that the therapeutic action is due to enhanced levels of interleukin-4 and -10 which down regulate the $T_H1$ pathway of the immune system which plays a significant role in the pathogenesis of inflammatory and autoimmune disorders. Furthermore interleukin-4 and -10 down regulate the expression of COX-2 leading to a decreased formation of inflammatory prostaglandins and a reduction of symptoms of acute inflammation. The therapeutic action may be relevant to all known autoimmune or inflammatory diseases and the following examples are not limiting with respect to this: Autoimmune hepatitis, Primary biliary cirrhosis, Primary sclerosing cholangitis, Autoimmune hemolytic anemias, Grave s disease, Myastenia gravis, Type 1 Diabetes Mellitus, Inflammatory myopathies, Multiple sclerosis, Hashimoto's thyreoiditis, Autoimmune adrenalitis, Crohn Disease, Ulcerative Colitis, Glomerulonephritis, Progressive Systemic Sclerosis (Scleroderma), Sögren's Disease, Lupus Erythematosus, Primary vasculitis, Reumatoid Arthritis, Juvenile Arthritis, Mixed Connective Tissue Disease, Atopic Dermatitis, Psoriasis, Pemfigus, Pemfigoid, Dermatitis Herpetiformis, etc.

The preferred embodiment of the invention is an extract of *Parthenium integrifolium*. Extracts according to the invention can i.a. be obtained by extraction or by steam or vacuum distillation of fresh or dried *Parthenium integrifolium* or parts thereof, preferably the root. Extraction may be performed with a number of different organic solvents, preferably water miscible solvents, and mixtures thereof with water. The extraction can be performed hot or cold by the employment of any extraction technology e.g. maceration, percolation or supercritical extraction.

The preferred extraction solvents are acetone, methyl ethyl ketone, ethyl acetate, lower alkanols having 1 to 4 carbon atoms and mixtures thereof with water. The preferred extraction temperature is close to the boiling point of the employed solvent due to extraction efficacy, but lower temperatures are also applicable making necessary a longer period of extraction.

By changing the composition of the applied solvent the extraction can be made more selective for certain constituents of *Parthenium integrifolium* thus enhancing or reducing their content in the finished extract. For example the content of phenolic glycosides can be increased by employing a more hydrophilic solvent while the content of sesquiterpenes in the finished product can be enhanced by employing a more lipophilic solvent.

After the primary extraction process a second step of processing, such as liquid-liquid extraction, column chromatography, steam distillation or vacuum distillation, can be employed to remove or to concentrate and possibly isolate any constituent of the extract. Hereby any constituent of *Parthenium integrifolium* can be avoided or concentrated in the finished extract, e.g. pyromeconic acid, sesquiterpene lactones like tetraneurin E and tetraneurin C, sesquiterpene esters like echinadiol cinnamate, epoxy echinadiol cinnamate, echinaxanthol cinnamate and dihydroxynardol cinnamate, flavonoids like quercetagetin methyl ethers and their O-glycosides, coumarins or various phenolic glycosides. Thus the content of any component of *Parthenium integrifolium* can be standardised in the finished extract for the purpose of manufacturing a pharmaceutical composition.

According to the invention *Parthenium integrifolium* or parts thereof or an extract or component thereof can be combined with any other active ingredient or plant extract to potentiate the therapeutic action. Consequently, we propose to combine *Parthenium integrifolium* or parts thereof or extracts or components thereof with eicosapentaenoic acid from fish oils or γ-linolenic acid for the treatment of inflammatory or autoimmune disorders. As a parallel, we propose to combine *Parthenium integrifolium* or parts thereof or extracts or components thereof with *Zingiber officinale* or parts thereof or extracts or components thereof for the treatment of pain and inflammation.

Furthermore it is obvious that in the use according to the invention for preparing medicines *Parthenium integrifolium* or parts thereof or an extract or component thereof may be mixed with additives such as surfactants, solvents, thickeners, stabilisers, preservatives, antioxidants, flavour etc. to obtain a desirable product formulation. Similarly, the pharmaceutical compositions according to the invention may further contain such additives. There are no limitations to the dosage form of the formulation, but tablets, gelatine capsules, fluids or granulates are envisaged. Optionally, the composition may also contain surfactants such as bile salts or polyoxyethylene-sorbitan-fatty acid esters for improving dispersibility of the composition in the digestive fluids leading to improved bioavailability or for obtaining the final dosage form of the composition.

EXAMPLES

Example 1

An extract of *Parthenium integrifolium* according to the invention was prepared as follows:

100 g dried root of *Parthenium integrifolium* was extracted with 1500 ml of boiling 90% ethanol for 4 hours. Thereafter the extract was filtered and evaporated to dryness under vacuum. Thus 22 g of an amber-coloured crystalline extract was obtained suitable for the manufacture of tablets or hard gelatine capsules.

Example 2

An extract of *Parthenium integrifolium* according to the invention was prepared as follows:

100 g dried root of *Parthenium integrifolium* was extracted with 1500 ml of boiling 96% ethanol for 5 hours. Thereafter the extract was filtered and evaporated to dryness under vacuum. 15 g of an amber-coloured crystalline extract was obtained. This *Parthenium integrifolium* extract was diluted in 30 ml 80% ethanol, and to this was added 15 g of acetylated monoglyceride and 5 g of polyoxyethylene-sorbitan-monooleate (Tween 80). Thus a liquid extract was obtained suitable for the manufacture of soft gelatine capsules.

Example 3

Materials and Methods

Mice

BALB/c mice, 5–6 weeks old were purchased from Gl. Bomholtgaard, Ry, Denmark. Unless otherwise specified they were fed standard food pellets and water ad libitum.

Test Compound (Extract of *Parthenium integrifolium*)

An extract of *Parthenium integrifolium* according to the invention was prepared as follows:

100 g dried root of *Parthenium integrifolium* was extracted with 1500 ml of boiling 80% ethanol for 3 hours. Thereafter the extract was filtered and evaporated to dryness under vacuum. Thus 24 g of an amber-coloured crystalline extract was obtained. This *Parthenium integrifolium* extract is abbreviated PI in the rest of this example.

Feeding Regime

Mice were fed crushed ordinary mouse pellets and water ad libitum. Crushed mouse pellets were exposed to PI or placebo: An ethanolic solution of PI was prepared and mixed with crushed standard mouse pellet. After drying the content of PI was 6 mg/kg mouse pellet. A mouse was estimated to consume 5 g standard mouse pellet a day resulting in a daily intake of 0,30 mg PI corresponding to a daily dosage of 10 mg/kg at an average body weight of 30 g/mouse. The control diet was prepared by substituting the PI ethanolic solution with pure ethanol in the above mentioned procedure.

Reagents

Sheep red blood cells (SRBC) were purchased from Statens Seruminstitut, Copenhagen Denmark. Antibodies for Elisa assay were purchased from Pharmingen, San Diego, Calif., U.S.A (see below). The SRBC were washed three times in physiological saline prior to use.

SRBC plaque forming cells (SRBC-PFC)

Four days after intravenous injection of 0.2 ml 10% SRBC in physiological saline, the mice were sacrificed and their spleens removed and homogenised by pressing the organs gently through a metal net. The cells were counted and mixed with SCRB and rabbit complement, and the cell mixture transferred to a reaction chamber (Cunningham and Stzenberg) for quantitation of SRBC-PFC. Four individual assay chambers were counted per splenocyte preparation. The numbers of PFC were calculated as numbers per $10^6$ splenocytes.

Anti-SRBC Antibody Titres

Mice were injected intraperitoneally with 10% SRBC in physiological saline in a volume of 0.5 ml. One hundred ml blood were collected from the retroorbital venous plexus at day 3, 6 and 9 post immunisation and transferred to vials containing 100 ml saline with 2 units of heparin. Plasma (50% dilution) was recovered by centrifugation and serial dilutions performed in round bottom microtitre plates (Nunc,Roskilde, Denmark). SRBC 0.1% and freshly diluted rabbit complement (Glapco, Jylland, Denmark) was added and the plates were incubated at 37° C. for 2 hours. Hemolysin titers of individual plasma samples were read by eye as the highest plasma dilution giving total lysis of the added SRBC.

Mixed Lymphocyte Culture (MLC)

Spleen cells obtained from pools of 5 spleens were cultured in volumes of 10 ml ($2\times10^6$) per ml in 25 ml T flasks and stimulated with irradiated C57BL6 splenocytes ($10^6$/ml). One ml culture supernatants were removed at day 3 and 4 of culture for cytokine determination.

Cytokines Secreted by MLC Responder Cells

Elisa assays for IL-2, IL-4 and IL-10 were set up using reagents from Pharmingen: IL-2 standard 1921IU, IL-4 standard1923IW and IL-10 standard 1228IV. Antibodies: anti-IL-2 18161D, anti-IL4 18031D and anti-IL-10 18141D (capture Abs), anti-IL-2 18172D, anti-IL-4 18042D and anti-IL-10 18152D (biotinylated detection Abs). Dose-response cytokine standard curves were generated. The three different cytokines secreted by the MLC responder cells at day 3 and 4 of culture were determined from replicate dilutions of the MLC culture supernatants. The linear part of the standard cytokine curves were used to determine the amounts of the individual cytokines.

Statistics

Wilcoxon rank sum test for paired differences and Fischers exact test were used for comparing anti-SRBC antibody titers and SRBC-PFC numbers respectively in PI and placebo fed mice.

Results

Both PI and placebo fed animals tolerated crushed mouse pellets well and no weight loss was registered in any of the experimental or placebo treated mice.

SRBC-PFC

The individual numbers of SRBC-PFC per $10^6$ splenocytes of two groups of 21 mice were derived from three separate experiments. The mice were fed PI or placebo for ten consecutive days and immunised with SRBC at day 6 and killed at day 10 of the feeding regime. The mean numbers of SRBC-PFC per $10^6$ splenocytes in the two groups were 400 and 220, respectively. However, these numbers were not statistically different (p>0.05, Wilcoxon). However, some differences among the two groups of mice were encountered. Thus, six of the 21 mice in the PI fed group and only 1 of 21 mice in the placebo group produced more than 500 PFC per $10^6$ splenocytes, this difference between the two groups being significant (p<0.02, Ficher's exact test). Moreover, when the ten mice producing the highest number of SRBC-PFC in each of the two groups were compared the difference between these two high responding "subgroups" was significant (P<0.05,Wilcoxon).

Anti-SRBC hemolysins

The results from the SRBC-PFC study prompted us to examine the level of anti-SRBC antibody titers from individual mice fed for 14 days with PI or placebo respectively. Table 1 shows the results. The PI fed group of mice showed significantly higher (p<0.005) anti-SRBC titer values at day 6 after immunisation as compared with the placebo fed group of mice.

TABLE 1

Anti-SRBC hemolysin titres in mice fed EPC-10 or placebo for 12 days. Mice were immunized at day 3 and antibody titers determined 3, 6 and 9 days after immunization.

| Days post immunization | MICE FED WITH: | |
| --- | --- | --- |
| | PI | Placebo |
| 3 | 7 (0–18)* | 18 (0–36) |
| 6 | 691# (576–1152) | 245 (72–288) |
| 9 | 202 (144–288) | 115 (72–144) |

*Numbers in parentheses represent the range of titers in five individual mice
Significantly different from the placebo fed group, p<0.005 (Wilcoxon)

Cytokines

Supernatants from the MLC cultures described above were assayed for cytokine content at day 3 and 4 of culture. The amounts of IL-2, IL-4 and IL-10, respectively, were measured in the MLC supernatants by a sensitive ELISA technique. As shown in Table 2, at day 3 of culture, the MLC supernatants from PI fed mice contained two times more IL-2 and IL-10 and seven times more IL-4. At day 4 of culture supernatants from the PI fed mice contained three times more IL-10 and twice as much IL-4 compared with MLC supernatants of placebo fed animals.

TABLE 2

Amounts* of IL-2, IL-4 and IL-10 secreted by allo-stimulated splenocytes obtained from PI or placebo fed mice.

| | PI | | | Placebo | | |
| --- | --- | --- | --- | --- | --- | --- |
| Days | ng/ml | | pg/ml | ng/ml | | pg/ml |
| of MLC | IL-2 | IL-10 | IL-4 | IL-2 | IL-10 | IL-4 |
| 3 | 13.5 | 2.6 | 191 | 6.2 | 1.3 | 26 |
| 4 | 0.9 | 2.9 | 54 | 0.7 | 1.0 | 27 |

*Amounts of cytokine per ml culture supernatant produced by MLC responder cells from a pool of five spleens, numbers represent the means of two replicate cytokine measurements.

Example 4

Study Object

An extract of *Parthenium integrifolium* according to the invention was prepared as follows:

1000 g dried root of *Parthenium integrifolium* was extracted with 10 000 ml of boiling 90% ethanol for 4 hours. Thereafter the extract was filtered and evaporated to dryness under vacuum. Thus 216 g of an amber-coloured crystalline extract was obtained. Tablets containing 50 mg of the extract were prepared.

Study Summary

Background

The object of the study was to evaluate the prophylactic effect of the extract of *Parthenium integrifolium* on migraine headache in an open clinical trial.

Methods 16 migraine sufferers with a history of at least four incidences of migraine headache a month during the last six months were included in the study.

The study schedule consisted of four periods of four weeks. The first period served as a baseline, where no treatment was employed. In the second period a daily dosage of 4 tablets was employed. In the third period a daily dosage of 2 tablets was employed. In the fourth period a daily dosage of 4 tablets was employed. During the four periods all incidences of migraine headache were recorded.

Statistics

Wilcoxon rank sum test for paired differences was used for comparing the incidence of migraine headache in each of the three treatment periods with the incidence in the baseline period.

Findings

The mean incidence of migraine headache was 5,75 in period 1 (baseline). The mean incidence of migraine head-35 ache was 30% lower in period 2, 43% lower in period 3 and 57% lower in period 4 as compared to baseline. Period 4 was significantly different from baseline (p<0.05; Wilcoxon).

Interpretation

In this study the tested extract of *Parthenium integrifolium* was concluded to be a powerful remedy in the prophylaxis of migraine headache.

What is claimed is:

1. An extract of *Parthenium integrifolium*, obtained by extraction of the plant or parts thereof with a water miscible organic solvent or a mixture thereof with water.

2. An extract according to claim 1, obtained by extraction with a water miscible organic solvent selected from the group consisting of acetone, methyl ethyl ketone, ethyl acetate or lower alkanols having 1 to 4 carbon atoms.

3. A pharmaceutical composition comprising an extract of *Parthenium integrifolium* according to claim 1 and a pharmaceutically acceptable carrier.

4. A pharmaceutical composition comprising the *Parthenium integrifolium* extract of claim 1 together with γ-linolenic acid or eicosapentaenoic acid and a pharmaceutically acceptable carrier.

5. A pharmaceutical composition comprising the *Parthenium integrifolium* extract of claim 1 together with *Zingiber officinale* or parts thereof or an extract or component thereof and a pharmaceutically acceptable carrier.

6. A pharmaceutical composition comprising an extract of *Parthenium integrifolium* according to claim 2 and a pharmaceutically acceptable carrier.

* * * * *